US010288552B2

(12) United States Patent
Salo

(10) Patent No.: US 10,288,552 B2
(45) Date of Patent: May 14, 2019

(54) SEALING ARRANGEMENT AND SEALING METHOD OF A MEASURING DEVICE

(71) Applicant: Janesko Oy, Vantaa (FI)

(72) Inventor: Harri Salo, Vantaa (FI)

(73) Assignee: JANESKO OY, Vantaa (FI)

(*) Notice: Subject to any disclaimer, the term of this patent is extended or adjusted under 35 U.S.C. 154(b) by 0 days.

(21) Appl. No.: 15/603,165

(22) Filed: May 23, 2017

(65) Prior Publication Data
US 2017/0356840 A1 Dec. 14, 2017

(30) Foreign Application Priority Data

Jun. 9, 2016 (FI) .................................. 20165476

(51) Int. Cl.
| G01N 21/03 | (2006.01) |
| G01N 21/15 | (2006.01) |
| F16J 15/06 | (2006.01) |
| G01K 13/02 | (2006.01) |
| G01N 21/41 | (2006.01) |
| G01N 21/09 | (2006.01) |
| G01N 21/85 | (2006.01) |
| G01N 21/05 | (2006.01) |

(52) U.S. Cl.
CPC .............. *G01N 21/15* (2013.01); *F16J 15/06* (2013.01); *G01K 13/02* (2013.01); *G01N 21/09* (2013.01); *G01N 21/4133* (2013.01); *G01N 21/85* (2013.01); *G01K 2013/026* (2013.01); *G01N 21/05* (2013.01); *G01N 2021/151* (2013.01)

(58) Field of Classification Search
CPC ...... F16J 15/06; G01N 21/15; G01N 21/4133; G01K 13/02
See application file for complete search history.

(56) References Cited

U.S. PATENT DOCUMENTS

| 5,090,871 A | * | 2/1992 | Story | ..................... | F16L 23/167 |
| | | | | | 210/85 |
| 5,562,406 A | * | 10/1996 | Ooka | ..................... | F04D 13/024 |
| | | | | | 277/300 |
| 2002/0018200 A1 | | 2/2002 | Salo | | |
| 2003/0015840 A1 | * | 1/2003 | Davis | ..................... | F16J 15/004 |
| | | | | | 277/320 |
| 2004/0075218 A1 | * | 4/2004 | Heinzen | ............... | F16J 15/3296 |
| | | | | | 277/321 |
| 2005/0211281 A1 | | 9/2005 | Caderas | | |

(Continued)

FOREIGN PATENT DOCUMENTS

| WO | WO 2006/086682 A2 | 8/2006 |
| WO | WO 2007/072262 A2 | 6/2007 |

OTHER PUBLICATIONS

Finnish Search Report dated Dec. 9, 2016 for Application No. 20165476.

*Primary Examiner* — Gilbert Y Lee
(74) *Attorney, Agent, or Firm* — Buchanan Ingersoll & Rooney PC

(57) ABSTRACT

A sealing arrangement and method of a measuring device are disclosed, the measuring device having one or more measuring elements that have a surface in contact with a fluid being measured, a fluid chamber for the fluid being measured, and a seal to seal the joint between the fluid chamber and the measuring element. Flow channels have been formed in the measuring device to lead the rinsing fluid in contact with the seal.

18 Claims, 2 Drawing Sheets

(56) References Cited

U.S. PATENT DOCUMENTS

2006/0191571 A1    8/2006   Kattler et al.
2009/0100947 A1    4/2009   Page
2012/0118058 A1    5/2012   Rainer et al.

* cited by examiner

SEALING ARRANGEMENT AND SEALING METHOD OF A MEASURING DEVICE

BACKGROUND OF THE INVENTION

The invention relates to a sealing arrangement and sealing method of a measuring device.

The measuring and controlling of aggressive chemicals by automatic in-line measuring devices and actuators is well justified due to the dangerous nature and high cost of the chemicals. The challenge in the measuring devices of aggressive chemical is the connecting of an optical or other measuring element to the other mechanics and process in a leak-proof manner so that the liquid or gas being measured stays in the measuring vessel or burette and cannot make it inside the measuring device. It is difficult, even impossible, to seal aggressive chemicals, such as fluorhydric acid and sulphuric acid, because when the chemicals gasify their small molecules manage to penetrate the sealant.

In connection with aggressive chemicals, fluorelastomers and perfluoroelastomers are typically used, which withstand aggressive chemicals well without being damaged.

The problem with the arrangement described above is that the sealing materials allow gasses to go through them, which causes damage to the sensitive optical, mechanical, or electronic parts inside the measuring device.

BRIEF DESCRIPTION OF THE INVENTION

An object of the invention is thus to provide an arrangement and method so as to enable the aforementioned problems to be solved. The object of the invention is achieved by an arrangement and a method which are characterized by what is disclosed in the independent claims. Preferred embodiments of the invention are disclosed in the dependent claims.

The invention is based on a sealing arrangement of a measuring device. The measuring device comprises one or more measuring elements that have a surface in contact with the fluid being measured, a fluid chamber for the fluid being measured, and a seal to seal the joint between the fluid chamber and measuring element. Flow channels have been formed in the measuring device to lead a rinsing fluid in contact with the seal.

In the sealing method according to the invention, the measuring device comprises one or more measuring elements that have a surface in contact with the fluid being measured, a fluid chamber for the fluid being measured, and a seal to seal the joint between the fluid chamber and measuring element. Flow channels are formed in the measuring device, in which a rinsing fluid is led to be in contact the seal.

The advantage of the arrangement and method according to the invention is the chance to use sealing materials that are well-known and have been found to be good, without endangering the sensitive optical, mechanical, or electronic parts within the measuring device.

BRIEF DESCRIPTION OF THE FIGURES

The invention will now be described in more detail in connection with preferred embodiments and with reference to the accompanying drawings, in which.

DETAILED DESCRIPTION OF THE INVENTION

Figure 1:
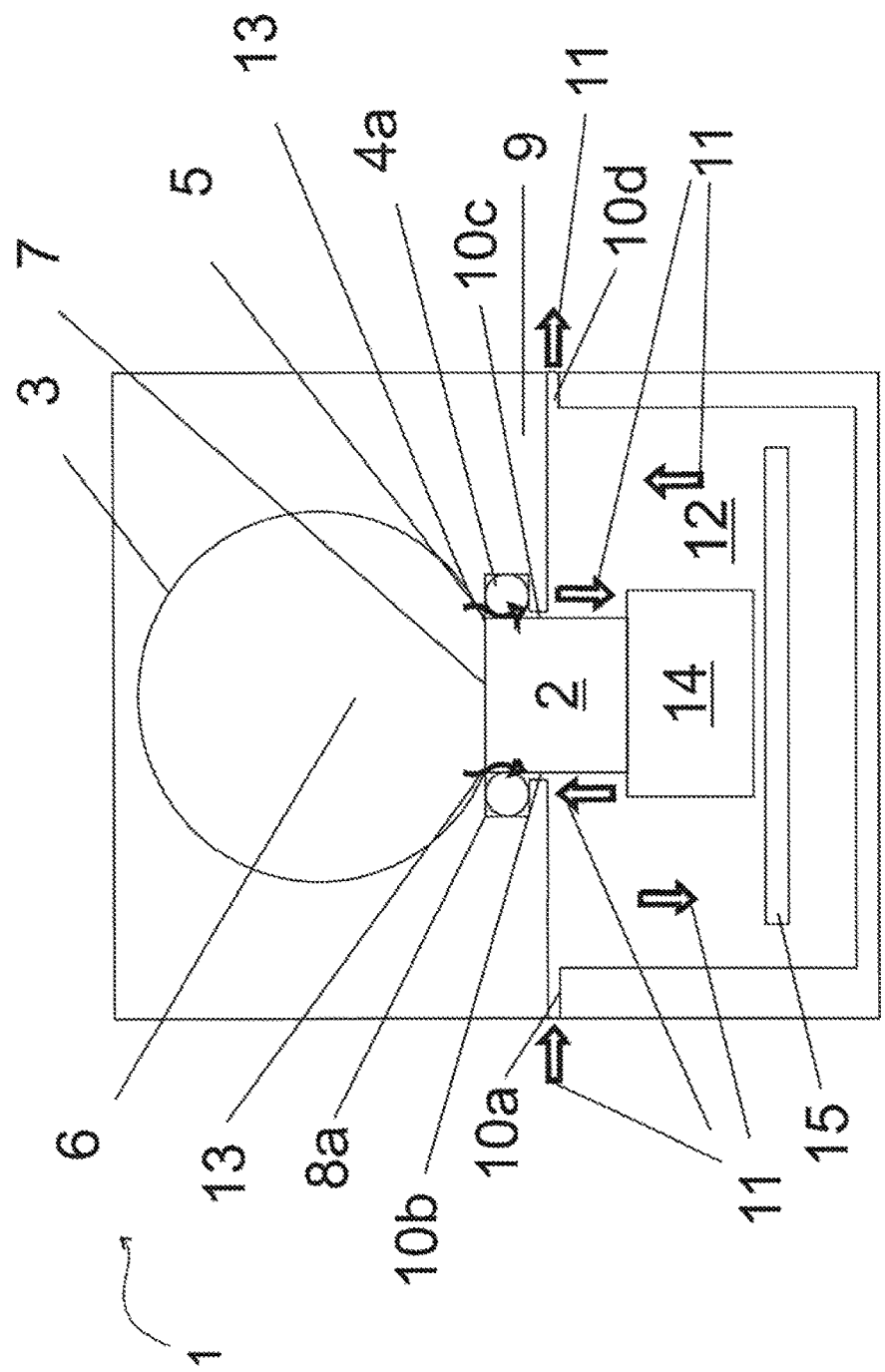
FIG. 1 shows a sealing arrangement of a measuring device.

FIG. 1 shows the first embodiment of the invention for a sealing arrangement of a measuring device. The measuring device 1 comprises a measuring element 2, a fluid chamber 3, and a seal 4a to seal the joint 5 between the fluid chamber 3 and measuring element 2.

Figure 2:
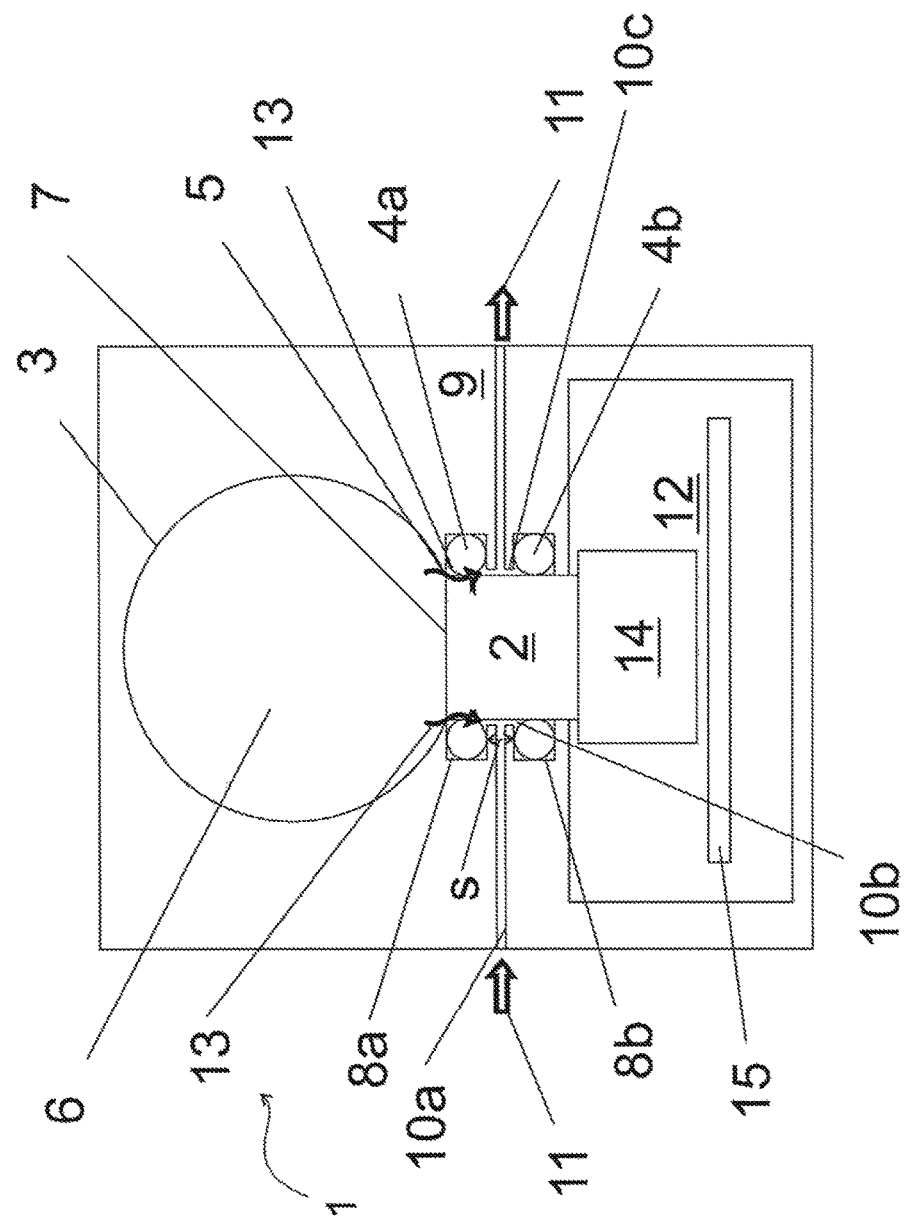
FIG. 2 shows a second sealing arrangement of a measuring device.

The measuring element 2 of FIGS. 1 and 2 is optical, electrical, or another measuring element 2 that has a surface 7 in contact with the fluid 6 being measured. The measuring element 2 may be a temperature measuring element, for example. It is further possible that the measuring device 1 comprises a plurality of measuring elements 2.

The fluid 6 to be measured is placed in the fluid chamber 3. In the Figures, the fluid chamber 3 is a flow pipe in which the fluid 6 being measured, such as a process liquid or gas, is flowing under pressure. The fluid chamber 3 may also be a container, for example, containing the fluid 6 being measured. In the Figures, the surface 7 in contact with the fluid 6 on the measuring element 2 forms a part of the wall of the fluid chamber 3.

The fluid 6 being measured is, for example, and aggressive chemical such as fluorhydric acid, ammonium hydroxide, phosphoric acid, or sulphuric acid. When the fluid 6 gasifies, the small molecules of the chemicals will penetrate the sealant.

The joint 5 between the fluid chamber 3 and measuring element 2 is sealed with a seal 4a. The seal 4a is placed away from the flow space of the fluid chamber 3 so that no protrusions would be formed in the flow space, which would interfere with the laminarity of the flow and would make measurements more difficult. The seal 4a is placed in the immediate vicinity of the joint surface 7 between the fluid chamber 3 and the measuring element 2. In the Figures, the seal 4a is placed in a groove 8a which is formed in a frame part 9 surrounding the measuring element 2. The seal 4a may also be placed in a groove formed on the outer wall of the fluid chamber 3.

Flow channels 10a-d have been formed in the measuring device 1 to lead a rinsing fluid 11 in contact with the seal 4a. The flow of the rinsing fluid 11 is illustrated by the arrows in the Figures. The rinsing fluid 11 flows in the measuring device through an inflow channel 10a. In the first embodiment, the flow channel or channels 10a-d of the rinsing fluid 11 are in a flow connection with the inner space 12 of the measuring device 1 in order to lead the rinsing fluid 11 also to the inner space 12. The rinsing fluid 11 flows both within the inner space 12 of the measuring device and around the seal 4a. In the first embodiment, the rinsing fluid 11 is advantageously a rinsing gas.

The flow channel 10b of the rinsing fluid 11 to the seal 4a, and the flow channel 10c from the from the seal 4a, are formed between the measuring element 2 and the frame part 9 surrounding the measuring element 2. The inflow channel 10a and the outflow channel 10d are arranged on the part of the seal 4a at the side of the measuring element 2 of the measuring device 1. The leaked gas 13, penetrated from the fluid chamber 3 through the seal 4a, is mixed with the rinsing fluid 11 and is removed with the rinsing fluid 11 from the surroundings of the seal 4a.

The rinsing fluid 11 flows out of the measuring device 1 through the outflow channel 10d. The rinsing fluid 11 led in the inner space 12 of the measuring device 1 protects the optical, mechanical, or electronic components within the inner space 12 at any one time, mixing into it the gas that may have leaked to the inner space. If the Figures, there are measuring components 14 and measuring electronics 15 within the measuring device.

In the Figures, the rinsing fluid 11 moves in the flow channel 10a-d by way of gravity or pressurised with a blower or compressor, for example. A minor pressurisation of the rinsing fluid 11 is advantageous, because it also reduces gas leaks through the seal 4a, because the pressure difference on the different sides of the seal 4a is smaller. The circulation of the rinsing fluid 11 may be open or closed depending on the space surrounding the measuring device 1. If the measuring device 1 is placed in a clean room, for example, in which the surroundings are well ventilated and the air is dry, open circulation may be used, in which the rinsing fluid 11 freely escapes the measuring device into the surrounding air. As the rinsing fluid 11, an inert gas, air, or, if the fluid is a gas, a fluid-absorbing gas or liquid may be used. The purpose of the rinsing fluid 11 is to purify the surroundings of the seal of leaked gas 13 that has leaked from the fluid chamber 3.

FIG. 2 shows a second embodiment of the invention.

In FIG. 2, the same reference numerals as in FIG. 1 are used at corresponding points. The measuring device 1 comprises a measuring element 2, a fluid chamber 3, and a seal 4a to seal the joint 5 between the fluid chamber 3 and measuring element 2.

The second embodiment makes use of two separate seals 4a-4b, to a space between which rinsing gas 11 is led to remove the leaked gas 13. In addition to the seal 4a presented in FIG. 1, the sealing arrangement uses a second seal 4b which is positioned at a distance s from the first seal 4a. The seals 4a-b are placed one after the other so that the second seal 4b is further away from the fluid chamber 3 than the first seal 4a. The rinsing fluid 11 is led to be in contact with both seals 4a-4b in order to purify the surroundings of both seals 4a-4b of the leaked gas 13.

In the second embodiment, the rinsing fluid 11 is advantageously a rinsing gas or rinsing liquid such as water. The rinsing liquid acts as a transporter of the leaked gas 13 and may additionally act as a cooling liquid, cooling the measuring device 1. In such a case, the temperature and flow rate is adapted to produce cooling power for the measuring device 1. When the rinsing liquid flows in the measuring device 1, with the measuring device 1 having a higher temperature than the rinsing liquid flowing through it, heat is transferred to the rinsing liquid that is flowing through. When the rinsing liquid is acting as a cooling liquid, too, it advantageously flows under pressure, and the flow rate of the rinsing liquid may be adjusted with the device producing the pressure. Cooling of the measuring device 1 is necessary in hot processes, for example.

In FIG. 2, the seal 4b is placed in a groove 8b which is formed in a frame part 9 surrounding the measuring element 2. The second seal 4b may also be placed in a groove formed on the outer wall of the fluid chamber 3, external to the flow space.

The flow channel or channels 10b of the rinsing fluid 11 to the seals 4a-b and the flow channel or channels 10c from the seals 4a-b are arranged between the first seal 4a and the second seal 4b. The flow channels to the seals 10b and from the seals 10c may also be arranged one after the other from the side of the second seal 4b, which is not opposite the first seal 4a, for example.

The flow channels 10a-d shown in the Figures may also be openings formed in the frame part 9 of the measuring device 1, whereby the rinsing fluid 11 flows by way of gravity. In such a case, the measuring device 1 is placed in a space where the surroundings are well ventilated and the humidity of the air that acts as the rinsing fluid 11 may be managed.

The flow channels 10a-d also act as leak detectors of the fluid chamber 3. If the seal 4a-b between the fluid chamber 3 and the measuring element 2 is damaged and fluid 6 seeps through past the seal 4a-b, the seeped fluid 6 accumulates in the flow channels 10a-d from which it is at least partly flushed off with the rinsing fluid 11.

The sealing arrangement of a measuring device set forth is well suited for a measuring device 1 used as a process monitoring device, which is connected to a process line in order to measure and/or control the characteristics of the process fluid.

The measuring device 1 shown in the Figures may be a refractometer, for example. An example of a prior art measuring device 1 to which the invention may be applied is the Semicon process refractometer PR-33-S. A refractometer is an optical measuring device used to measure the refractive index or a fluid. As a process monitoring device, a refractometer measures the content of substances dissolved in the process liquid by determining the refractive index of the fluid in contact with the measuring component, a prism. The measuring element of the refractometer is a measuring window and/or temperature sensor, for example. A refractometer additionally includes measuring components and measuring electronics within it. The measuring component is a light source, for example. The light source may be a suitable monochromatic light source, for example a laser diode. The measurement electronics may be, for example, a CCD element or camera, image analyser and the calibration electronics of the measuring device.

In the sealing method of a measuring device, the measuring device 1 comprises one or more measuring elements 2, a seal 4a-b, and a fluid chamber 3. In the method, the fluid 6 to be measured is arranged in the fluid chamber 3, and one or more measuring elements 2 of the measuring device 1 are made to contact the fluid 6 being measured through a surface 7 of the measuring element 2. The joint 5 between the fluid chamber 3 and the measuring element 2 is sealed with at least one seal 4a-b so that the fluid 6 may not leak out of the fluid chamber 3. Flow channels 10a-d are formed in the measuring device 1, by means of which a rinsing fluid 11 is led to be in contact the seal 4a-b. In the method, the leaked gas 13, penetrated from the fluid chamber 3 through the seal 4a-b, is mixed with the rinsing fluid 11 and is removed with the rinsing fluid 11 from the surroundings of the seal 4a-b and the measuring device 1.

A person skilled in the art will find it obvious that, as technology advances, the basic idea of the invention may be implemented in many different ways. The invention and its embodiments are thus not restricted to the above-described examples but may vary within the scope of the claims.

PARTS LIST 1 measuring device, 2 measuring element, 3 fluid chamber, 4a-b seal, 5 joint, 6 fluid, 7 surface, 8a-b groove, 9 frame part, 10a-d flow channel, 11 rinsing fluid, 12 inner space, 13 leaked gas, 14 measuring component, 15 measuring electronics.

s distance.

The invention claimed is:

1. A sealing arrangement of a measuring device, comprising in combination:

a measuring device having one or more measuring elements that have a surface for measuring and/or controlling characteristics of a fluid to be measured, said surface being arranged so as to contact the fluid to be measured;

a fluid chamber for the fluid being measured; and a seal to seal a joint between the fluid chamber and the one or more measuring elements, wherein flow channels have been formed in the measuring device to lead a rinsing fluid in contact with the seal for purifying the surroundings of the seal, said flow channels including an inflow channel for leading the rinsing fluid in the measuring device and an outflow channel for leading the rinsing fluid out from the measuring device.

2. A sealing arrangement as claimed in claim 1, wherein the inflow channel and the outflow channel are arranged on a part of the seal at a side of a measuring element of the measuring device.

3. A sealing arrangement as claimed in claim 2, wherein the arrangement comprises:

a second seal which is at a distance from the first seal, and arranged so that the rinsing fluid is to be led to be in contact also with the second seal.

4. A sealing arrangement as claimed in claim 3, wherein the flow channels to the seals and the flow channels from the seals are arranged between the seal and the second seal.

5. A sealing arrangement as claimed in claim 4, configured such that rinsing fluid will move in the flow channels by way of gravity or in a pressurised form.

6. A sealing arrangement as claimed in claim 5, wherein the inlet flow channel is in a flow connection with an inner space of the measuring device for leading the rinsing fluid to the inner space.

7. A sealing arrangement as claimed in claim 6, wherein the measuring element is a measuring window and/or a temperature sensor.

8. A sealing arrangement as claimed in claim 7, wherein the measuring device is a process monitoring device.

9. A sealing arrangement as claimed in claim 8, wherein the measuring device is a refractometer.

10. A sealing arrangement as claimed in claim 1, wherein the arrangement comprises:

a second seal which is at a distance from the first seal, and arranged so that the rinsing fluid is to be led to be in contact also with the second seal.

11. A sealing arrangement as claimed in claim 10, wherein the flow channels to the seals and the flow channels from the seals are arranged between the seal and the second seal.

12. A sealing arrangement as claimed in claim 1, configured such that rinsing fluid will move in the flow channels by way of gravity or in a pressurised form.

13. A sealing arrangement as claimed in claim 1, wherein the flow channel is in a flow connection with an inner space of the measuring device for leading the rinsing fluid to the inner space.

14. A sealing arrangement as claimed in claim 1, wherein the measuring element is a measuring window and/or a temperature sensor.

15. A sealing arrangement as claimed in claim 1, wherein the measuring device is a process monitoring device.

16. An arrangement as claimed in claim 1, wherein the measuring device is a refractometer.

17. A sealing method of a measuring device, the method comprising:

providing a measuring device with one or more measuring elements that have a surface for measuring and/or controlling characteristics of a fluid being measured, said surface being in contact with the fluid being measured, and a fluid chamber for the fluid being measured; and sealing a joint between the fluid chamber and the measuring element with a seal, wherein flow channels are formed in the measuring device to lead a rinsing fluid to be in contact with the seal for purifying the surroundings of the seal, said flow channels including an inflow channel for leading the rinsing fluid in the measuring device and an outflow channel for leading the rinsing fluid out from the measuring device.

18. A sealing method of a measuring device as claimed in claim 17, wherein the rinsing fluid is a rinsing liquid, the method comprising:

adapting a temperature and flow rate of the rinsing liquid to produce cooling power for the measuring device.

* * * * *